US00PP10574P

United States Patent [19]

Lambert

[11] Patent Number: Plant 10,574

[45] Date of Patent: Aug. 25, 1998

[54] AGLAONEMA PLANT NAMED 'MOONSHINE'

[75] Inventor: Marcus Steven Lambert, Zolfo Springs, Fla.

[73] Assignee: Sunshine Foliage World, Zolfo Springs, Fla.

[21] Appl. No.: 855,492

[22] Filed: May 13, 1997

[51] Int. Cl.[6] ..... A01H 5/00

[52] U.S. Cl. ..... Plt./88.1

[58] Field of Search ..... Plt./88.1

*Primary Examiner*—James R. Feyrer

*Assistant Examiner*—Kent L. Bell

*Attorney, Agent, or Firm*—C. A. Whealy

[57] ABSTRACT

A new and distinct cultivar of Aglaonema named 'Moonshine' particularly characterized by its horizontal growth habit; rapid growth rate; long and broad leaves; silvery green leaf surfaces without any green markings, spots or blotches typical of other Aglaonemas of this type; low temperature-tolerance; and exceptional disease-resistance.

2 Drawing Sheets

The present invention relates to a new and distinct cultivar of Aglaonema plant, botanically known as *Aglaonema commutatum var. picturatum* and hereinafter referred to by the cultivar name 'Moonshine'.

The new cultivar is a spontaneous mutation of the non-patented *Aglaonema commutatum var. picturatum* cultivar 'Alumina Armandia'. The new cultivar was discovered and selected in April, 1992, by the inventor in a controlled environment in Zolfo Springs, Fla., as a single sprout on a single plant among a population of plants of the cultivar 'Alumina Armandia'. Plants propagated from this sprout consistently have solid silver green leaves without dark green markings, spots or blotches; have a more horizontal growth habit; produce more sprouts at the base of the plant; and are more compact, denser and fuller compared to plants of the cultivar 'Alumina Armandia'.

Asexual propagation of the new cultivar at Zolfo Springs, Fla., has shown that the unique features of this new Aglaonema plant are stable and reproduced true to type in successive generations of asexual propagation.

The following traits have been repeatedly observed and are determined to be the unique characteristics of 'Moonshine'. These characteristics in combination distinguish 'Moonshine' as a new and distinct cultivar:

1. Plants of the new Aglaonema are horizontal in growth and produce sprouts freely.
2. Plants of the new Aglaonema have a rapid growth rate.
3. The leaves of the new Aglaonema are relatively long and broad.
4. The adaxial leaf surfaces of plants of the new Aglaonema are solid silver green without any dark green markings, spots or blotches typical of other Aglaonemas of this type.
5. Plants of the new Aglaonema are tolerant of low temperatures, that is, ambient temperatures of about 8° C. do not cause damage.
6. Plants of the new Aglaonema are exceptionally resistant to diseases common to Aglaonema.

The accompanying colored photographs illustrate the overall appearance of the new cultivar, showing the colors as true as it is reasonably possible to obtain in colored reproductions of this type.

The first photograph comprises a top perspective view of a typical single plant of 'Moonshine' in a 2-gallon container.

The second photograph comprises a close-up view of the adaxial surfaces of a young leaf (top) and fully mature leaf (bottom). Leaf colors in the photographs may appear different from the actual colors due to light reflectance.

The new Aglaonema has not been observed under all possible environmental conditions. The phenotype may vary somewhat with variations in environment such as temperature, light intensity and fertilizer rate, without, however, any variance in genotype. The following observations, measurements and comparisons describe plants grown in Zolfo Springs, Fla., under a polypropylene-covered shadehouse and conditions which closely approximate those used in horticultural practice. Plants were grown under day temperatures ranging from 21° to 38° C. and night temperatures ranging from 7° to 21° C. The polypropylene shade provided an 84 percent decrease in ambient light levels.

In the following description, color references are made to The Royal Horticultural Society Colour Chart except where general terms of ordinary dictionary significance are used.

Botanical classification: *Aglaonema commutatum var. picturatum* cultivar 'Moonshine'.

Parentage: Naturally-occurring mutation of *Aglaonema commutatum var. picturatum* cultivar 'Alumina Armandia'.

Propagation: By division and by cuttings.

Plant description:

*Plant shape.*—Outwardly spreading, broad inverted triangle, symmetrical. Numerous leaves and sprouts give plants a full, dense appearance.

*Growth habit.*—Erect when young, becoming more outwardly arching and spreading to horizontal as leaves develop.

*Plant size.*—Height: Soil surface to top of leaf canopy: About 40 cm. Width: About 90 cm.

*Plant vigor.*—Moderate to high, rapid growth rate.

*Root description.*—Thick, fleshy and fibrous. Time to initiate roots: About 10 and 20 days at soil temperatures of 29° and 16° C., respectively. Time to develop roots: About 14 and 30 days at soil temperatures of 29° and 16° C., respectively.

*Stem description.*—Diameter at soil surface: About 2.5 cm. Internode length: About 2 cm. Color: 146A.

*Foliage description.*—Leaf shape: Oval. Leaf length, fully expanded: About 27.5 cm. Leaf width, fully expanded: About 11.5 cm. Margin: Entire. Leaf surface: Flat. Leaf tip: Acuminate. Leaf base: Cordate. Leaf aspect: Erect initially, then mature leaves held horizontally to the stem. Leaf texture: Leathery, smooth, glabrous. Leaf color: Young, adaxial surface: Closest to 147B, glossy. Young, abaxial surface: 147B to 146B, dull. Mature, adaxial surface: Closest to 191A–D, dull. Mature, abaxial surface: 147A to 146B, dull. Petiole length, primary shoot: About 26 cm. Petiole diameter, primary shoot, at apex: About 7 mm. Petiole diameter, primary shoot, at base: About 1.5 cm. Petiole wing, primary shoot: Apparent on lower 55 to 60% of mature leaf petiole. Petiole wing, primary shoot: Length: About 14 cm. Width: About 8 mm. Petiole color: Young: 144A to 146B. Mature: Winged area: Closest to 146A. Above winged area: Closest to 146A. Venation: Adaxial surface: Closest to 191A, slightly sunken. Abaxial surface: 146B to 144A, prominent.

*Inflorescence.*—Typical of Aglaonema, no commercial significance.

Disease tolerance: Plants of the new Aglaonema are exceptionally resistant to diseases common to Aglaonema.

Low temperature tolerance: Plants of the new Aglaonema are tolerant of low temperatures, that is, ambient temperatures of about 8° C. do not cause damage.

It is claimed:

1. A new and distinct cultivar of Aglaonema plant named 'Moonshine', as illustrated and described.

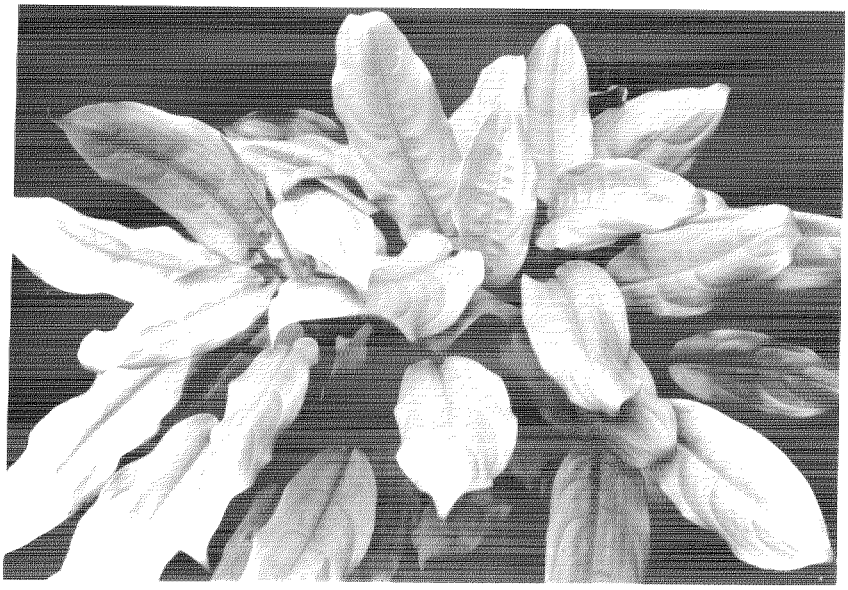

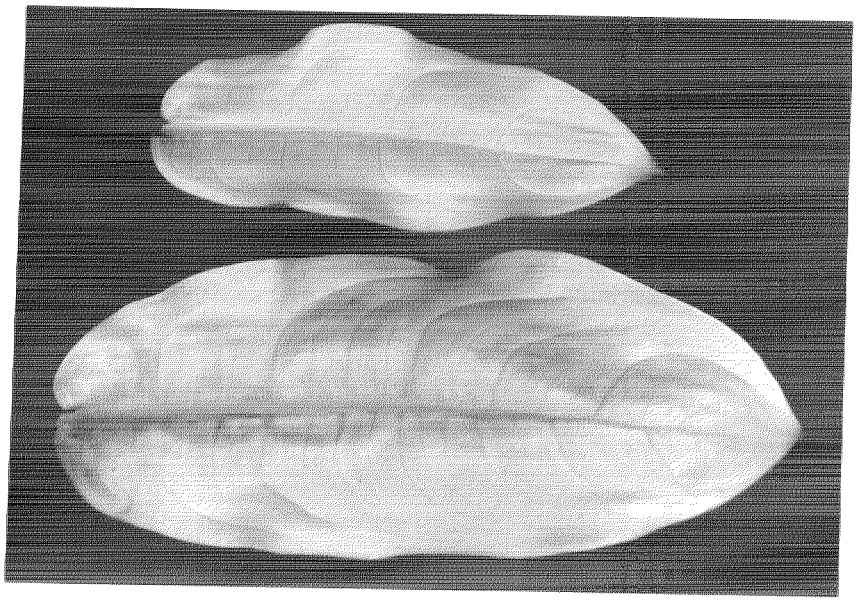

* * * * *